United States Patent [19]

Kohne

[11] Patent Number: 4,851,330

[45] Date of Patent: Jul. 25, 1989

[54] METHOD FOR DETECTION, IDENTIFICATION AND QUANTITATION OF NON-VIRAL ORGANISMS

[76] Inventor: David E. Kohne, 364 Nautilus St., La Jolla, Calif. 92037

[21] Appl. No.: 40,737

[22] Filed: Apr. 16, 1987

Related U.S. Application Data

[63] Continuation of Ser. No. 456,729, Jan. 10, 1983, abandoned.

[51] Int. Cl.$^4$ .......................... C12Q 1/68; C12Q 1/22; C12Q 1/18; C12Q 1/06; C12P 19/34; C12N 15/00; G01N 33/48; G01N 33/00; G01N 33/567

[52] U.S. Cl. .......................................... 435/6; 435/91; 435/172.1; 435/31; 435/32; 435/39; 430/63; 430/94; 430/504; 935/78

[58] Field of Search ................ 435/6, 91, 172.1, 172.3, 435/320, 317.1, 31, 32, 34, 35, 39, 259, 820; 536/27; 436/63, 94, 504; 935/78

[56] References Cited

U.S. PATENT DOCUMENTS

| | | | |
|---|---|---|---|
| 4,302,204 | 11/1981 | Wahl et al. | 435/6 |
| 4,358,535 | 11/1982 | Falkow et al. | 435/6 |
| 4,699,877 | 10/1987 | Cline et al. | 435/6 |

OTHER PUBLICATIONS

Fox et al.: Int. J. Syst. Bacteriol. 27, 44 (1977).
Brenner et al.: J. Bacteriol. 129, 1435 (1977).
Woese: Scientific American 244(6), 98 (1981).
Wirth et al.: Proc. Natl. Acad. Sci. U.S.A. 79, 6999 (1982).
Deisseroth et al.: Somatic Cell Genetics 2, 373 (1976).
Kennell: Progr. Nucl. Acid Res. Mol. Biol. 11, 259 (1971).
Repeated Sequences in DNA.
R. J. Britten and D. E. Kohne, Science (1968) 161 p. 529.
Kinetics of Renaturation of DNA.
J. C. Wetmur and N. Davidson, J. Mol. Biol. (1968) 31 p. 349, Hydroxyapatite Techniques for Nucleic Acid Reassociation.
D. E. Kohne and R. J. Britten, in Procedures in Nucleic Acid Research (1971), eds. Cantoni and Davies, Harper and Row vol. 2, p. 500.
Hybridization of Denatured RNA and Small DNA Fragments Transferred to Nitrocellulose.
P. S. Thomas, Proc. Natl. Acad. Sci. U.S.A. (1980) 77 p. 5201.
DNA-DNA Hybridization on Nitrocellulose Filters: General Considerations and Non-Ideal Kinetics.
R. Flavell et al., Eur. J. Biochem. (1974) 47 p. 535.
Assay of DNA-RNA Hybrids by $S_1$ Nuclease Digestion and Adsorption to DEAE-Cellulose Filters.
I. Maxwell et al., Nucleic Acids Research (1978) 5 p. 2033.
Efficient Transcription of RNA into DNA by Avian Sarcoma Virus Polymerase.
J. Taylor et al., Biochemica et Biophys. Acta (1976) 442 p. 324.
Use of Specific Radioactive Probes to Study Transcription and Replication of the Influenza Virus Genome.
J. Taylor et al., J. Virology (1977) 21 #2, p. 530.
Virus Detection by Nucleic Acid Hybridization: Examination of Normal and ALs Tissue for the Presence of Poliovirus.
D. Kohne et al., Journal of General Virology (1981) 56 pp. 223-233.
Leukemogenesis by Bovine Leukemia Virus.
R. Kettmann et al., Proc. Natl. Acad. Sci. U.S.A. (1982) 79 #8 pp. 2465-2469.
Prenatal Diagnosis of α Thalassemia: Clinical Application of Molecular Hybridization.
Y. Kan et al., New England Journal of Medicine (1976) 295 #21 pp. 1165-1167.
Use of Synthetic Oligonucleotides as Hybridization Probes.
S. V. Suggs et al., Proc. Natl. Acad. Sci. U.S.A. (1981) 78 p. 6613.
Identification of Enterotoxigenic *E. coli* by Colony Hydridization Using 3 Enterotoxin Gene Probes.
S. L. Mosely et al., J. of Infect. Diseases (1982) 146 #6 p. 863.
DNA Reassociation in the Taxonomy of Enteric Bacteria.
D. Brenner, Int. J. Systematic Bacteriology (1973) 23 #4 pp. 298-307.
Comparative Study of Ribosomal RNA Cistrons in Enterobacteria and Myxobacteria.
R. Moore et al., J. Bacteriology (1967) 94 pp. 1066-1074.
Ribosomal RNA Similarities in the Classification of Rhodococcus and Related Taxa.

(List continued on next page.)

*Primary Examiner*—James Martinell

[57] ABSTRACT

A method for specifically and sensitively detecting, identifying, and quantitating any non-viral organism, category or group of organisms containing ribosomal RNA in a sample is disclosed. The nucleic acids of the organisms present in the sample are brought together with a marked probe comprising nucleic acid molecules which are complementary only to ribosomal RNA subsequences known to be conserved in an organism, category or group or organisms. The probe and sample nucleic acid mixture is incubated under nucleic acid hybridization conditions and then assayed to determine the degree of hybridization that has occurred. Hybridization indicates the presence and identity of the organism, category or group or organisms in the sample. The quantity of ribosomal RNA present in the sample can be determined and compared to that normally present in the known organisms to determine the number of organisms present. Batteries of sequentially more specific probes can also be utilized.

28 Claims, No Drawings

OTHER PUBLICATIONS

M. Mordarski et al., J. General Microbiology (1980) 118 pp. 313-319.
Retention of Common Nucleotide Sequences in the Ribosomal RND DNA of Eukaryotes and some of their Physical Characteristics.
J. Sinclair et al., Biochemistry (1971) 10 p. 2761.
Homologies Among Ribosomal RNA and Messenger RNA Genes in Chloroplasts, Mitochondria and *E coli*.
H. Bohnert et al., Molecular and General Genetics (1980) 179 pp. 539-545.
Heterogeneity of the Conserved Ribosomal RNA Sequences of *Bacillus subtilis*.
R. Doi et al., J. Bacteriology (1966) 92 #1 p. 88.
Isolation and Characterization of Bacterial Ribosomal RNA Cistrons.
D. Kohne, Biophysical Journal (1968) 8 #10 pp. 1104-1118.
Taxonomic Relations between Archaebacteria Including 6 Novel Genera Examined by Cross-Hybridization of DNAs and 16S R-RNAs.
J. Tu et al., J. Mol. Evol. (1982) 18 p. 109.
R-RNA Cistron Homologies among *Hyphomicrobium* and Various other Bacteria.
R. Moore, Canadian J. Microbiology (1977) 23 p. 478.
Amikam, et al., "Ribosomal RNA Genes in Mycoplasma", *Nucleic Acids Research* 10: 4215 (1982).
Sugino et al., "Partial Nucleotide Sequence Similarity within Species of *Mycoplasma* and *Acholeplasma*", *J. Gen. Micro.* 121: 333 (1980).
Bendich and McCarthy, "Ribosomal RNA Homologies among Distantly Related Organisms," *Proc. Nat. Acad. Sci.*, 65:349-356 (1970).

METHOD FOR DETECTION, IDENTIFICATION AND QUANTITATION OF NON-VIRAL ORGANISMS

This is a continuation of co-pending application Ser. No. 456,729 filed on Jan. 10, 1983, now abandoned.

BACKGROUND OF THE INVENTION
1. Field of the Invention

The present invention relates to a method and means for detecting, identifying, and quantitating non-virus organisms in biological and other samples. More particularly the present invention relates to a method for specifically and sensitively detecting and quantitating any organism containing ribosomal RNA, hereinafter rRNA: any members of large, intermediate, or small sized categories or taxonomic groups of such organisms; and previously unknown organisms containing rRNA. The method is capable of detecting the presence of even one organism containing rRNA.

My invention has broad application to any area in which it is important to detect the presence or absence of living organisms. Such areas include medical, veterinary, and agricultural diagnostics, and industrial and pharmaceutical biological quality control.

The invention involves a method of using specifically produced nucleic acids complementary to rRNA, hereinafter rRNA probes, to detect, quantitate, and identify specific rRNA sequences by a procedure which includes nucleic acid hybridization as an essential step.

My invention and the novelty, utility, and unobviousness thereof can be more clearly understood and appreciated when considered in the light of the representative background information hereinafter set out, comprising this art.

Each of the cells of all life forms, except viruses, contain ribosomes and therefore ribosomal RNA. A ribosome contains three separate single strand RNA molecules, namely, a large molecule, a medium sized molecule, and a small molecule. The two larger rRNA molecules vary in size in different organisms.

Ribosomal RNA is coded for by the rRNA gene. This DNA sequence is used as a template to synthesize rRNA molecules. A separate gene exists for each of the ribosomal RNA subunits. Multiple rRNA genes exist in most organisms, many higher organisms containing both nuclear and mitochondrial rRNA genes. Plants and certain other forms contain nuclear, mitochondrial and chloroplast rRNA genes. For simplicity of discussion hereinafter, the three separate rRNA genes will be referred to as the rRNA gene.

Numerous ribosomes are present in all cells of all life forms. About 85–90 percent of the total in RNA in a typical cell is rRNA. A bacterium such as *E. coli* contains about $10^4$ ribosomes per cell while a mammalian liver cell contains about $10 \times 10^6$ ribosomes. Since each ribosome contains one of each rRNA subunit, the bacterial cell and mammalian liver cell contains $10^4$ and $5 \times 10^6$, respectively, of each rRNA subunit.

Nucleic acid hybridization, a procedure well-known in the art, has been used in the prior art to specifically detect extremely small or large quantities of a particular nucleic acid sequence, even in the presence of a very large excess of non-related sequences. Prior art uses of nucleic acid hybridization are found, for example, in publications involving molecular genetics of cells and viruses; genetic expression of cells and viruses; genetic analysis of life forms; evolution and taxonomy of organisms and nucleic acid sequences; molecular mechanisms of disease processes; diagnostic methods for specific purposes, including the detection of viruses and bacteria in cells and organisms.

Probably the best characterized and most studied gene and gene product are the rRNA gene and rRNA, and the prior art includes use of hybridization of rRNA and ribosomal genes in genetic analysis and evolution and taxonomic classification of organisms and ribosomal gene sequences. Genetic analysis includes, for example, the determination of the numbers of ribosomal RNA gene in various organisms; the determination of the similarity between the multiple ribosomal RNA genes which are present in cells; determination of the rate and extent of synthesis of rRNA in cells and the factors which control them. Evolution and taxonomic studies involve comparing the rRNA gene base sequence from related and widely different organisms.

It is known that the ribosomal RNA gene base sequence is at least partially similar in widely different organisms, and that the DNA of *E. coli* bacterial ribosomal RNA genes hybridizes well with rRNA from plants, mammals, and a wide variety of other bacterial species. The fraction of the *E. coli* gene which hybridizes to these other species varies with the degree of relatedness of the organisms. Virtually all of the rRNA gene sequence hybridizes to rRNA from closely related bacterial species, while less hybridizes to rRNA from distantly related bacterial species, and even less with mammalian rRNA.

2. Description of the Prior Art

I am not aware of any prior art which teaches my method of detecting the presence or absence of rRNA characteristic of a particular group of organisms utilizing nucleic acid hybridization wherein is used a selected marked nucleic acid molecule complementary to a subsequence of rRNA from a particular source. Nor am I aware of any prior art which discloses my method for detecting the presence or absence of rRNA in general by nucleic acid hybridization using a marked nucleic acid molecule complementary to all of the rRNA subsequences from a specific source.

While the presence of organisms can be detected by any one of a large variety of prior art methods, none of these is entirely satisfactory for one reason or another. Such methods include, e.g., growth methods, optical detection methods, serologic and immunochemical methods, and biochemical methods, and are further discussed hereinafter.

Growth Tests

A large number of different growth tests exist, each useful for the growth of a specific organism or group of organisms. Growth tests have the potential sensitivity to detect one organism. In practice, however, many organisms are difficult or impossible to grow. These tests are usually lengthy, taking from one day, to months, to complete. In addition, a very large number of tests would be needed to detect the presence of any member of a large group of organisms (e.g., all bacteria), assuming that the growth conditions for all members of the group are known.

Optical Detection Methods

Microscopic analysis coupled with differential staining methods is a very powerful, and in many cases, very rapid detection method. A major problem with this approach is the detection of specific organisms in the presence of large quantities of other organisms, for example, the identification of a specific type of gram negative rod shaped bacteria, in the presence of many different kinds of gram negative rod shaped bacteria. In addition, a large number of tests would be needed to detect the presence of all members of a large group of organisms (such as the group of all bacteria).

Serologic and Immunochemical Methods and Biochemical Tests

A large number of different types of these tests exist. They are ususally qualitative, not very sensitive and often require a growth step. A great many of these tests would be required to detect all members of a large group of organisms.

SUMMARY OF THE INVENTION

My invention is a simple method and means having, as characterizing qualities, (a) the ability to specifically detect the presence of any one of a large number of different organisms with a single assay procedure, which also works regardless of the pattern of genetic expression of any particular organism; (b) the ability to modify the test to detect only specific categories of organisms, even in the presence of organisms not in the group of interest; (c) extremely high sensitivity of detection, and ability to detect the presence of one organism or cell; (d) the ability to quantitate the number of organisms or cells present; and (e) does not require a growth step.

As described hereinbefore, rRNA base sequences are partially similar in widely different organisms. The more closely related two organisms are, the larger the fraction of the total rRNA which is similar in the two species. The rRNA sequence of any particular species of organism can be regarded as a series of short rRNA subsequences, of which one subsequence is similar in virtually all life forms. Therefore, the rRNA of almost all life forms must contain this subsequence. A different subsequence is similar only in the rRNA of the members of the Species to which that organism belongs. Other subsequences are present in the Order of organisms that the Species belongs to, and so on.

Because the rRNA sequences of widely different organisms are at least partially similar, the method of my invention, using a probe which detects the rRNA sequences which are similar in widely different organisms, can detect the presence or absence of any one or more of those organisms in a sample. A marked nucleic acid sequence, or sequences complementary to the rRNA sequences similar in widely divergent organisms, can be used as such a probe in a nucleic acid hybridization assay.

Because the rRNA sequences of closely related organisms are more similar than those of distantly related organisns, the method of my invention, which includes using a probe which detects only the rRNA sequences which are similar in a particular narrow group of organisms, can detect the presence or absence of any one or more of those particular organisms in a sample, even in the presence of many non-related organisms. These group specific probes can be specific for a variety of different sized categories. One probe might be specific for a particular taxonomic Genus, while another is specific for a particular Family or another Genus.

Group specific probes have the ability to hybridize to the rRNA of one group of organisms but not hybridize to the rRNA of any other group of organisms. Such a group specific complementary sequence will detect the presence of rRNA from any member of that specific group of organisms even in the presence of a large amount of rRNA from many organisms not belonging to that specific group.

The total number of rRNA molecules in a sample is measured by using a marked sequence or sequences complementary to rRNA and standard excess probe or excess sample RNA nucleic acid hybridization methodology.

The rRNA content of cells from a wide variety of organisms is known in the art. In a broad group of similar organisims, for example bacteria, the amount of rRNA per cell varies roughly 2-5 fold. Therefore, if the number of rRNA molecules in a sample, and the broad class identity of the source of the rRNA is known, then a good estimate of the number of cells present in the sample can be calculated. If the broad class identity is not known it can be determined by hybridizing the sample to a series of selected probes complementary to rRNA, each of which is specific for a particular broad category of organisms.

At the present time, the operational detection and quantitation range of a single assay procedure is from $10^4$ rRNA molecules (1 bacterium or $10^{-2}$ mammalian cells) to about $10^{12}$ rRNA molecules ($10^8$ bacteria or $10^6$ mammalian cells) a span of about $10^8$ in cell numbers. A single test could also be done in such a way as to operationally quantitate from $10^3$ bacteria to $10^{10}$ bacteria. The test is quite flexible in this way.

Because the test for rRNA is specific and has the ability to detect the presence of very few organisms there is no need to amplify the numbers of organisms through a growth step.

The practice of that form of my invention which is directed to determining the presence of an organism which contains rRNA, in a sample which might contain such organism, comprises basically:
 (a) bringing together the sample, or isolated nucleic acids contained in that sample, with a probe which comprises marked nucleic acid molecules which are complementary to the rRNA of all organisms;
 (b) incubating the resulting mixture under predetermined hybridization conditions for a predetermined time, and then;
 (c) assaying the resulting mixture for hybridization of the probe.

When my invention is directed to determining the presence of any member of a specific category of organisms which contain rRNA in a sample which might contain such organisms, the method comprises:
 (a) contacting the sample, or the nucleic acids therein, with a probe comprising marked nucleic acid molecules which are complementary only to the rRNA of members of the specific category of organisms, but not complementary to rRNA from non-related organisms;
 (b) incubating the probe and the sample, or the isolated nucleic acids therein; and
 (c) assaying the incubated mixture for hybridization of said probe.

My invention can also be used to determine the number of organisms present in the sample under investigation, by adding to the assaying in the second above described method in the event probe hybridization has occurred, the step of comparing the quantity of rRNA present in the sample with the number of rRNA molecules normally present in individual organisms belonging to the said specific group.

And, of course, included in the variations, within the scope of my invention, which can be used, is that which comprises, in lieu of the single probe of step (a) in the second of the above methods, a multiplicity or battery, of different probes. In such case, each separate probe comprises marked nucleic acid molecules which are complementary only to the rRNA of a specific group of organisms and each probe is specific for a different group of organisms; step (a) is followed by incubating each probe-sample mixture under predetermined hybridization conditions for a pre-determined time, and then assaying each mixture for hybridization of the probe.

PROCEDURES FOR THE PRODUCTION OF GROUP SPECIFIC rRNA PROBES

Different approaches can be used to produce group specific probes. All of these approaches but one, rely on differential nucleic acid hybridization methods to identify and purify the group specific probe sequences.

Procedure A

The most useful procedure for producing group specific rRNA probes uses recombinant DNA methodology. The steps involved in this procedure follow: (The specific details of standard DNA recombinant techniques are described in the book, *Molecular Cloning, A Laboratory Manual*, T. Maniatis et al., Cold Spring Harbor Publication (1982).)

1. Isolate nucleic acid from a specific organism of interest. Standard isolation methods are used.

2. Using this isolated DNA, clone the rRNA genes of this organism and then produce large amounts of the ribosomal gene DNA, using standard DNA recombinant technology, as shown in Maniatis et al., supra.

3. Reduce the rRNA gene DNA to short pieces with restriction enzymes and make a library of these short DNA pieces, using standard DNA recombinant methods, as shown in Maniatis et al., supra.

4. Screen the library and identify a clone which contains a short rRNA gene sequence which hybridizes only to rRNA from other members of the taxonomic Species of the organism of interest. Isolate this clone. It contains a Species specific DNA sequence which is complementary only to the rRNA of the specific Species to which the organisms of interest belongs.

Screen the library further and identify and isolate the following clones: (a) a clone which contains a DNA sequence complementary to rRNA which will only hybridize to rRNA from members of the taxonomic Genus to which the organism of interest belongs; (b) a clone which contains a DNA sequence complementary to rRNA which will only hybridize to rRNA from members of the taxonomic Order to which the organism of interest belongs; (c) a clone which contains a DNA sequence complementary to rRNA which will hybridize only to rRNA from members of the taxonomic Family to which the organism of interest belongs; (d) a clone which contains a DNA sequence complementary to rRNA which will hybridize only to rRNA from members of the taxonomic Class to which the organism of interest belongs; and (e) a clone which contains a DNA sequence complementary to rRNA which will hybridize to rRNA from as many different life forms as possible.

The foregoing clone selection scheme is only one of a number of possible ones.

Standard methods of cloning and screening are to be utilized, as discussed in Maniatis et al., supra.

5. (a) Produce large amounts of each clone's DNA. From the DNA of each individual clone isolate and purify only the DNA sequence which is complementary to rRNA, using one of the many methods existing to accomplish this, e.g., as in Maniatis et al., supra.

(b) In certain instances the total DNA present in a clone is useful as a probe, in which case the total DNA isolated from the cloning vector is used.

(c) In certain other instances, the DNA single strand of the cloning vector which contains the DNA sequence complementary to rRNA is used as a probe. In such case this strand must be isolated and purified, using one of the various methods which exist to accomplish this, as described by Maniatis et al.

6. The probe DNA obtained in 5a, 5b, and 5c must be marked in some way so that it can be identified in the assay mixture. Many different kinds of markers can be used, the most frequently used marker being radioactivity. Others include fluorescence, enzymes and biotin. Standard methods are used for marking the DNA, as set out in Maniatis et al., supra.

7. The group specific rRNA gene sequence in the cloning vector exists in a double strand state. One of these strands is complementary to rRNA and will hybridize with it. The other strand will not hybridize to rRNA but can be used to produce marked group specific sequences complementary to rRNA. This is done by utilizing a DNA or RNA polymerase and nucleic acid precursor molecules which are marked. The enzyme will utilize the marked precursors for synthesizing DNA or RNA using the DNA strand as a template. The newly synthesized marked molecule will be complementary to rRNA and can be used as a group specific probe. The template DNA can be removed by various established means leaving only single strand marked nucleic acid, as described in Maniatis, et al., supra, and the article by Taylor et al., in Biochemica and Biophys. Acta (1976) 442, p. 324.

Procedure B

Several enzymes can utilize rRNA from any source as a template for the synthesizing of marked DNA complementary to the entire rRNA sequence. Group specific sequences complementary only to the rRNA of a particular class of organisms can be isolated by a hybridization selection process. The fraction of the synthesized marked DNA which hybridizes only to the rRNA from members of a specific class of organisms can be isolated by standard hybridization procedures. An example of this process is presented hereinafter.

Procedure C

The nucleotide sequences of rRNA from widely different organisms has been determined. Group specific sequences similar to a specific group of organisms can be identified by comparing these known sequences. A sequence complementary to this group specific rRNA sequence can then be chemically synthesized and marked, using standard methodology.

Isolation of Sample Nucleic Acid

Standard methods are used to isolate the nucleic acid from the samples to be assayed; in certain instances nucleic acid hybridization can be done without isolating the nucleic acid from the sample. An example of one standard method of nucleic acid isolation is presented in the examples and also discussed in Maniatis et al., supra.

The Nucleic Acid Hybridization Test

Nucleic Acid Hybridization: Two basic methods for performing nucleic acid hybridizations are available. In one, in solution hybridization, both the probe and sample nucleic acid molecules are free in solution. With the other method the sample is immobilized on a solid support and the probe is free in solution. Both of these methods are widely used and well documented in the literature. An example of the in solution method is presented hereinafter in the examples. Also, in the article by Thomas et al., Proc. Natl. Acad. Sci. USA (1980), 77 p. 520, is described an immobilization method.

Performing the Nucleic Acid Hybridization

An appropriate amount of marked probe is mixed with the sample nucleic acid. This mixture is then adjusted to a specific salt concentration (NaCl is usually used) and the entire mix incubated at a specific temperature for a specific time period. At the end of the time period the mixture is analyzed by performing a hybridization assay. Many different combinations of salt, solvent, nucleic acid concentrations, volumes and temperature exist which allow nucleic acid hybridization. The preferred combination depends upon the circumstances of the assay. It is important, however, that the criteria (see "Definitions") of the hybridization steps be identical to criteria used to identify and select the group specific probe. If the criteria of the hybridization step are different, the probe specificity may change. See: "Repeated Sequences in DNA", by Britten and Kohne, Science (1968) 161 p. 529; "Kinetics of Renaturation of DNA", by Wetmur and Davidson; J. Mol. Biol. (1968) 31 p. 349; "Hydroxyapatite Techniques for Nucleic Acid Reassociation", by Kohne and Britten; Procedures in Nucleic Acid Research (1971), eds. Cantoni and Davies, Harper and Row, Vol. 2, p. 500.

Two different approaches are used with regard to the amount of probe and sample nucleic acid present in the hybridization mixture. In one, the excess probe method, there is more probe present than sample nucleic acid, in this case rRNA. With the other, the excess rRNA method, there is more rRNA present than probe. The excess probe method is the method of choice for detecting the presence of rRNA in unknown samples. It has several advantages which are discussed below. See Tables 2 and 3 for further discussion of these two approaches.

Using the excess probe method, the detection and quantitation can be done with just one lab assay point, if the proper rRNA probe is available. If the hybridization has gone to completion the amount of probe which has hybridized is a direct measure of the amount of rRNA present in the sample. The fact that the probe hybridizes at all indicates that rRNA is present, and the amount of probe which hybridizes indicates the amount of rRNA present in the sample.

Making sure that the hybridization has gone to completion in a known time is important in order to quantitate the rRNA. This is readily done by adding enough probe to ensure that the hybridization goes to completion in a selected time period. The more probe added, the faster completion is reached. Thus the excess probe method provides a means to ensure that the hybridization has gone to completion and to know when this has occurred.

In contrast, the detection and quantitation of rRNA can't be done with one lab assay point when using the excess rRNA method. In addition, the time when the test point should be taken cannot be predicted in the excess rRNA method. Unknown samples with small amounts of rRNA will hybridize much more slowly than samples with large amounts of rRNA.

THE ASSAY FOR HYBRIDIZATION

Quantitation of rRNA

The signal that rRNA of the specific group is in the sample is the presence of double strand marked probe. Many different methods are available for assaying the hybridization mixture for the presence of marked probe in the double strand form. These methods are well documented in the literature. The choice of method depends upon the method chosen for the hybridization step, the composition of the hybridization mixture, the type of marker on the probe and other factors. One commonly used method is described hereinafter. See also Wetmur and Davidson, Kohne and Britten, and Thomas et al., supra. Also the article by Flavell et al., Eur. J. Biochem. (1974) 47 p. 535. And also, the article by Maxwell et al., Nucleic Acids Research (1978) 5 p. 2033.

In all cases, however, it is important to either assay at or above the same criterion used for the hybridization reaction or at a criterion at which hybridization cannot occur.

The quantity of rRNA present in a sample can be determined in several ways by nucleic acid hybridization, using methods well known to the art. One commonly used method is disclosed hereinafter.

It will be understood that the present method is applicable in any case it is necessary to determine the presence or absence of organisms which contain rRNA and that such includes biological samples such as sputum, serum, tissue swabs, and other animal fluids and tissues as well as industrial and pharmaceutical samples and water.

TABLE 1

EXCESS SELECTED PROBE METHOD

PROBE: The probe is a specific, selected, marked sequence from a member of bacteria group B, which represents 10 percent of the base sequence of the rRNA, and hybridizes completely with rRNA from group B bacteria, but does not hybridize with rRNA from other organisms. The probe cannot hybridize with itself.

A. Positive Homologous Control 0.1 micrograms Probe +  → Hybridize to completion and  → (a) One percent of the probe will form
                       assay for double strand probe.     double strand molecules.

$10^{-3}$ micrograms Sample group B rRNA                      (b) This is a direct measure of the rRNA in the sample. The number of probe molecules hybridized equals the number of rRNA molecules present.

B. Heterologous Control

TABLE 1-continued
EXCESS SELECTED PROBE METHOD

PROBE: The probe is a specific, selected, marked sequence from a member of bacteria group B, which represents 10 percent of the base sequence of the rRNA, and hybridizes completely with rRNA from group B bacteria, but does not hybridize with rRNA from other organisms. The probe cannot hybridize with itself.

| | | |
|---|---|---|
| 0.1 micrograms Probe + <br><br> $10^{-3}$ micrograms Sample human rRNA | → Hybridize to completion and assay for double strand probe. | → The probe does not hybridize with any rRNA but rRNA from group B bacteria. |
| C. Unknown Sample <br> 0.1 micrograms Probe + <br><br> Unknown sample | → Hybridize to completion and assay for double strand probe | → (a) If no group B rRNA is present, no probe will hybridize. <br> (b) If group B rRNA is present, the probe will hybridize and form double strand molecules. <br> (c) The number of probe molecules hybridized equals the number of group B rRNA molecules present in the sample. <br> (d) If one percent of the probe hybridizes, group B rRNA is present since the probe was selected so that it would hybridize only with rRNA from group B bacteria. Since the probe will only hybridize to group B rRNA, the presence of other rRNAs will not interfere the detection or the quantitation of any bacterial rRNA present <br> (e) Using a selected probe makes it easier to ensure that the hybridization is complete. A selected probe representing 10 percent of the rRNA sequence will hybridize 10 times faster than a probe which is representative of the total rRNA sequence. <br> (f) The detection of rRNA in general is not possible since the probe hybridizes only with group B rRNA. The sensitivity of detection of group B rRNA is extremely high. |
| | D. Summary <br> The excess probe method needs just one assay point in order to detect and quantitate group B organisms. | |

TABLE 2
EXCESS rRNA METHOD: THE USE OF A SELECTED PROBE

PROBE: The probe is a specific, selected, marked sequence from group B bacteria, which represents one-tenth of the rRNA base sequence of one member of group B. The probe hybridizes completely with rRNA from group B, but does not hybridize to rRNA from other organisms. The probe cannot hybridize with itself

| | | |
|---|---|---|
| A. Positive Homologous Control <br> Sample 0.1 micrograms Group B rRNA + <br><br> $10^{-3}$ micrograms Probe | → Hybridize to completion and assay for double strand probe. | → (a) The fraction of probe which hybridizes is a direct measure of the similarity between the rRNA and the probe. In this case 100 percent of the probe can hybridize. <br> (b) This percentage is not a measure of the amount of rRNA present. In order to determine this the kinetics of the reaction must be determined. |
| B. Heterologous Control <br> Sample 0.1 micrograms human rRNA + <br><br> Probe $10^{-3}$ micrograms | → Hybridize to completion and assay for double strand probe | → The probe does not hybridize to non-bacterial rRNAs. |
| C. Unknown Sample <br> Sample + <br><br> Probe $10^{-3}$ micrograms | → Hybridize to completion and assay for double strand probe. | → (a) If no group B rRNA is present in the sample there will be no hybridized probe. <br> (b) If group B rRNA is present the probe will be hybridized. <br> (c) The amount of rRNA can't be determined from the percentage hybridization at the completion of the reaction. In order to determine this the kinetics of the hybridization must be determined. Since the probe will hybridize with only |

TABLE 2-continued
EXCESS rRNA METHOD: THE USE OF A SELECTED PROBE

PROBE: The probe is a specific, selected, marked sequence from group B bacteria, which represents one-tenth of the rRNA base sequence of one member of group B. The probe hybridizes completely with rRNA from group B, but does not hybridize to rRNA from other organisms. The probe cannot hybridize with itself one type of rRNA, the kinetic determination is simple.

(d) If 100 percent of the probe has hybridized with the sample, this means that group B rRNA is present in the sample. It does not indicate that only this rRNA is present. Other rRNAs which do not hybridize with the probe may also be present in the sample.

(e) If 100 percent of the probe hybridizes with the sample, it is possible to specifically quantitate the group B rRNA in the presence of human rRNA by determining the kinetics of hybridization of the probe with the sample rRNA. Since the probe will hybridize only with group B rRNA such a kinetic reaction will have only one component, the one from reacting with group B rRNA.

(f) There are situations where the hybridization can't go to completion. In this method the sample rRNA must drive the hybridization to completion, since only a very small amount of probe is present. If there is not sufficient rRNA in the sample, the hybridization will not be completed. The interpretation of such a situation is discussed below.
If hybridization of unknown sample results in 20 percent hybridization of the probe at the usual assay time, it is not possible to tell if the reaction is complete with only one time-point. It is necessary to take another point at double the original time to determine if the hybridization value increases. If it does not increase then the hybridization is complete. In this case the rRNA is at such low concentration in the sample that the probe is in excess, and the number of rRNA molecules present in the sample is equal to the number of probe molecules hybridized. If the hybridization value is increased the hybridization was not over at the first time-point. A third time-point must then be done to determine whether the reaction was over at the second time point.

D. Summary
The excess sample rRNA method needs multiple assays points in order to detect and quantitate, and is much more time-consuming than the excess probe method Use of Selected Probes Complementary to Only a Particular Fraction of the rRNA Sequence from a Particular Source to Detect rRNA Versus Use of Unselected Probes Complementary to the Entire rRNA Sequence from a Particular Source to Detect rRNA One aspect of my invention, which comprises using specifically selected probes complementary to only a particular fraction of the rRNA sequences to detect, quantitate, and identify rRNA has important capabilities and advantages over another aspect of the invention, that of using unselected probes or sequences complementary to the entire rRNA sequence to detect rRNA. The advantages of using a selected probe in both excess rRNA and excess probe hybridization methodologies are set forth below. The problems with using a completely representative probe are also presented.

The advantages of using a selected probe over using a completely representative rRNA probe, with excess probe hybridization, as well as with excess rRNA hybridization, is set out below:

| Advantages of the Excess Probe Hybridization Method | |
|---|---|
| Problems with Completely Representative rRNA Probe | Advantages of Using Selected Probes |
| 1. rRNA can be detected in a sample with the excess probe method but there is no way of determining the type of rRNA present. Thus this probe cant't be used to specifically detect and quantitate the presence of a particular rRNA in an unknown sample, with the excess probe hybridization method. | The selected probe can be used to sensitively and specifically detect and quantitate the presence of a particular rRNA, in an unknown sample when used in an excess probe hybridization method. This can be done with just one lab assay, even in the presence of rRNA from other organisms. |
| 2. As stated above, the excess probe method cannot be used with this probe to detect or quantitate the presence of a particular rRNA in a sample. For this purpose the probe must be used in the excess rRNA method. The excess rRNA method is much more time consuming, requires much more work, and is much more complicated than the excess probe method. | The use of a selected probe makes it possible to use the excess probe method for detecting and quantitating the presence of a particular rRNA in an unknown sample. This greatly simplifies the task. |
| 1. rRNA can be detected in an unknown sample with this probe, but in many cases there is no way of determining the type or quantity of rRNA which is present. Thus in many instances the probe cannot be used to specifically detect and quantitate the presence of a particular rRNA in an unknown sample | The selected probe can be used to specifically detect and quantitate the presence of a particular rRNA in an unknown sample in all situations. This can be done even in the presence of large amount rRNA from other organisms. |
| 2. In many cases the sensitivity of detection of a specific rRNA is limited by the presence of rRNA from other organisms. | With the selected probe the presence of rRNA from other organisms does not lower the sensitivity of detection of a particular rRNA. |
| 3. In many cases where it is possible to detect and quantitate the presence of particular rRNA, it requires a lot of work | The detection and quantitation of the presence of a particular rRNA is much easier when a selected probe is utilized |

ILLUSTRATIVE EMBODIMENT

My invention, illustratively, may be used to determine whether a tissue culture cell line, or a human or other mammalian tissue, is contaminated with any bacteria-like organisms.

In a typical situation, about $10^6$–$10^7$ mammalian cells are grown in a tissue culture plate at one time. Bacterial species, especially members of the taxonomic Class Mollicutes, are known to contaminate tissue culture cells. Members of the Class Mollicutes, unlike most other bacteria, are not readily eliminated by antibiotics, and are troublesome contaminants of cell cultures. Many different Mollicutes species have been detected in tissue culture cells. If just one of these organisms is present in the culture plate, it has the potential, even in the presence of antibiotics, to multiply and produce hundreds of organisms per cell. Such organisms are capable of altering the activity of cells, thereby affecting the results of various studies, and the marketability of cell culture products.

Prior art methods for detecting these organisms involve basically qualitative tests, the most commonly used being growth tests, differential staining tests and immunologic assays. The growth tests, while quite sensitive, take 3–6 weeks. They have the additional disadvantage that many organisms are difficult or impossible to grow.

While the actual detection sensitivity of the staining method is not known, it is known that more than several organisms per cell have to be present.

Immunologic tests are qualitative tests and involve using antibody toward a particular species. While they can be carried out rapidly, they are not very sensitive; furthermore, many different antibodies would be required to detect all types of Mollicutes.

The embodiment of applicant's method described in Example I, below, is a test which may be used to detect and quantitate the presence of any member of the group of all bacteria, including the taxonomic Class Mollicutes, to detect the presence of Mollicutes in tissue culture, to detect the presence of bacteria in tissue which is normally free of bacteria, and to detect the presence of the bacteria even in the presence of large numbers of mammalian cells.

As set forth in the example, applicant's method involves first making a specific rRNA probe which is complementary to rRNA from any bacteria but is not complementary to mammalian cell rRNA. The use of such a probe in a nucleic acid hybridization test allows the detection of any bacteria type, even in the presence of large numbers of mammalian cells.

A detailed description of this embodiment of the invention follows:

EXAMPLE I

Preparation of rRNA from Mammalian and Bacterial Cells

Mammalian cells are resuspended in 0.3 M NaCl, 0.02 M Tris, pH=7.4. Sarkosyl is added to a final concentration of 1 percent to lyse the cells. Immediately upon lysis an equal volume of a 1/1 mixture of phenol/chloroform is added and the resulting mixture shaken vigorously for 2 minutes. The mixture is then centrifuged (8000 x for 10 minutes) to separate the aqueous and organic phases. The aqueous phase is recovered, and to this is added another volume of phenol/chloroform. After shaking and centrifugation as above, the aqueous phase is again recovered. To this is added 2 volumes of 95% ethanol and this mixture is placed at $-20°$ C. for 2 hours to facilitate precipitation of the nucleic acids. Then the mixture is centrifuged (8000 x g, 10 minutes) in order to sediment the precipitate to the bottom of the tube. The liquid is then removed. The pelleted nucleic acid is redissolved in water. This solution is then made to 0.2 M NaCl, $5 \times 10^{-3}$ M MgCl$_2$, $5 \times 10^{-3}$ M CaCl$_2$. 0.02 M Tris (pH=7.4), 50 micrograms per ml of deoxyribonuclease I and incubated at 37° C. for 1 hour. Then add an equal volume of phenol/chloroform and shake as above. Centrifuge as above and recover the aqueous phase. Ethanol precipate the RNA as above. Centrifuge the precipitate as above and redissolve the pelleted RNA in water. Make this solution to 2 M LiCl and place it at 4° C. for 10–20 hours in order to facilitate the precipitation of the high molecular weight RNA. Then centrifuge this solution to collect the precipate and redissolve the precipitate in water. This preparation of RNA contains greater than 95% rRNA.

Bacterial rRNA is isolated in a similar manner with the following exceptions. In those cases where detergent alone does not lyse the bacteria, other means are employed. This usually involves pretreating the bacteria with an enzyme (lysozyme) to make them susceptible to lysis by sarkosyl. After lysis of the bacteria the isolation procedure is as described above.

Purified rRNA is stored at $-70°$ C.

Production of Radioactive DNA Complementary ($^3$H-cDNA) to Mollicutes rRNA rRNA from the species *Mycoplasma hominis* (*M. hominis*), a member of the taxonomic class Mollicutes, is used as a template to synthesize radioactive cDNA complementary to *M. hominis* rRNA.

This cDNA is produced by utilizing the ability of an enzyme, reverse transcriptase, to utilize rRNA as a template and produce $^3$H-cDNA complementary (cDNA) to rRNA. The reverse transcriptate reaction mixture contains the following: 50 mM Tris·HCl (pH=8.3), 8 mM MgCl$_2$, 0.4 mM dithiothreitol, 50 mM KCl, 0.1 mM $^3$H-deoxythymidinetrephosphate (50 curies per millimole), 0.2 mM deoxyadenosintriphosphate, 0.2 mM deoxycytidinetriphosphate, 0.2 mM deoxyguanosinetriphosphate, 200 micrograms per ml of oligodeoxyribonucleotide primer made from *E. coli* DNA, 50 micrograms per ml of *M. hominis* rRNA and 50 units per ml of AMV reverse transcriptase. This mixture is incubated at 40° C. for 30 minutes. Then ethylene diamine tetraacetic acid (EDTA) (pH=7.3), sodium dodecyl sulfate (SDS), NaCl and glycogen are added to final concentrations of $10^{-2}$M, 1 percent, 0.3 M, and 100 micrograms per ml respectively. The solution is then mixed with 1 volume of phenol/chloroform (1/1) and shaken vigorously for 2 minutes, then centrifuged (8000 x g for 10 minutes) and the aqueous phase recovered. The nucleic acids are precipitated by the addition of 2.5 volumes of 95% ethanol. The precipitate is recovered by centrifugation and redissolved in H$_2$O. This solution contains the template rRNA and the newly synthesized $^3$H-cDNA.

This solution is then, made to 0.3 M NaOH and incubated at 50° C. for 45 minutes, and cooled in ice and neutralized with 0.3 M HCl. Two and one-half volumes of 95% EtOH are then added to precipitate the remaining nucleic acid and the resulting precipitate redissolved in water. This solution is then passed over a Sephadex G-100 column equilibrated to 0.3 M NaCl, 0.1 percent sarkosyl and the excluded volume recovered. This solution is ethanol precipitated and the resulting precipitate redissolved in a small volume of water. The process described in this paragraph removes the template rRNA and any remaining precursor material from the $^3$H-cDNA preparation.

The $^3$H-cDNA is then hybridized to *M. hominis* rRNA to ensure that it is indeed complementary to this rRNA. The hybridization mixture consists of, 0.05 micrograms of single strand $^3$H-cDNA, 20 micrograms of *M. hominis* rRNA, and 0.48 M PB (phosphate buffer) in 1 ml. This mixture is incubated for 0.2 hours at 65° C. and is then diluted to 0.14 M PB and passed over a hydroxyapatite (HA) column equilibrated to 0.14 M PB and 65° C. $^3$H-cDNA hybridized to rRNA adsorbs to the hydroxyapatite (HA) column while non-hybridized $^3$H-cDNA passes through the column. The hybridized $^3$H-cDNA is then recovered by elution of the HA column with 0.3 M PB. The fraction is then dialysed to remove the PB, ethanol precipitated to concentrate the nucleic acid, centrifuged and the nucleic acid redissolved in water. The solution is then treated with NaOH as described above in order to remove the rRNA. After neutralization, addition of glycogen carrier and concentration by ethanol precipitation, the $^3$H-cDNA is redissolved in a small volume of water. This solution contains only $^3$H-cDNA which is complementary to *M. hominis* rRNA.

Selection of $^3$H-cDNA Which is Complementary to *M. hominis* rRNA but is not Complementary to Human rRNA The purified $^3$H-cDNA is further fractionated by hybridizing it with a great excess of human rRNA. The hybridization mixture consists of 0.05 micrograms $^3$H-cDNA, and 40 micrograms of human rRNA in one ml of 0.48 M PB. This is incubated at 68° C. for 1 hour and the mixture is then diluted to 0.14 M PB and passed over HA equilibrated to 55° C. and 0.14 M PB. The fraction (about 50% of the total) which does not adsorb to the HA (i.e., $^3$H-cDNA not hybridized to human rRNA) is collected. This fraction is repassed over a new HA column under the same conditions. Again the non-adsorbed fraction is collected. This fraction is dialysed to remove the PB, ethanol precipitated to concentrate the nucleic acid and redissolved in water. This solution is treated with NaOH, as described earlier, in order to remove the human rRNA. After neutralization, addition of glycogen carrier, and concentration by ethanol precipitation, the $^3$H-cDNA is redissolved in a small volume of water. This ³H-cDNA preparation is complementary to *M. hominis* rRNA but is not complementary to human rRNA.

Hybridization of Selected ³H-cDNA with rRNA from Different Sources

The production of the selected ³H-cDNA probe allows the detection of bacteria, including members of the Class Mollicutes in mammalian tissue culture cells and mammalian tissues by detecting the presence of bacterial rRNA by nucleic acid hybridization. A necessary requirement of such a test is that the selected probe must not hybridize to rRNA from mammalian cells which do not contain bacteria. That this requirement is met is shown in Table 4V.

Table 4, parts II and III show that the probe will detect all members of the class Mollicutes and should detect all types of bacteria. For example, *Legionella p.* and *E. coli* and *Bacillus subtilis* are representatives of very different bacterial types and the probe hybridizes with rRNA from each of these types. Evolutionary considerations indicate that this probe will hybridize to rRNA from virtually any known or unknown bacteria. This is due to the extreme conservation of the rRNA nucleotide sequences during evolution.

This selected probe is useful for detecting the presence of a specific Class of bacteria, Mollicutes, in tissue culture cells. In most tissue culture cells antibiotics are present in the growth medium and this prevents the growth of virtually all bacteria but members of the Class Mollicutes. Thus any contamination of a tissue culture preparation is almost certain to be due to a member of the Class Mollicutes.

An important aspect is the ability to determine the number of organisms present. In most cases, cell lines and their products are discarded when cells are shown, by prior art methods, to be contaminated. The ability to quantitate these organisms makes it possible to make judgements as to the severity of any effects due to contamination. The degree of a contamination may be very light, and only one organism per 1000 cells present. This level of contamination would have very little effect on the cells and in many situations the cell products need not be discarded. The decision might be made to retain valuable cell lines until they become more heavily contaminated. Quantatitive considerations are important for judging the importance of any kind of a bacterial contamination.

TABLE 4

Hybridization of Selected Mollicutes ³H—cDNA with rRNA from Widely Different Sources

| | | Source of rRNA | Percent Hybridization of ³H—cDNA with rRNA |
|---|---|---|---|
| I. Control Experiments | A. | No rRNA added, Self Reaction of ³H—cDNA | <1% |
| | B. | Mock rRNA isolation | <1% |
| | C. | Human cell RNA known to be contaminated *M. hominis* rRNA | 97% |
| II. Hybridization of ³H—cDNA with rRNA from different species of the taxonomic Class Mollicutes | A. | Members of the Order Mycoplasmatales | |
| | | 1. *Mycoplasma hominis* (infects humans) | 97% |
| | | 2. *Mycoplasma salivarium* (infects humans) | 93% |
| | | 3. *Mycoplasma hyorhinis* (infects pigs) | 84% |
| | | 4. *Mycoplasma pulmonis* (infects mice) | 82% |
| | B. | Members of the Order Acholeplasmataceae | |
| | | 1. *Acholeplasma laidlawii* isolate #1 (infects cows, birds, dogs, house cats, mice, sheep, pigs and primates) | 52% |
| | | 2. *Acholeplasma laidlawii* isolate #2 | 53% |
| II. | C. | Members of the Order Spiroplasmataceae | |
| | | 1. SMCA (infects insects and mice) | 69% |
| | | 2. Honey bee (isolated from honey bee) | 68% |
| | | 3. Cactus (isolated from cactus) | 71% |
| | | 4. Corn Stunt (isolated from corn) | 69% |
| | | 5. Corn Stunt (isolated from insect) | 65% |
| III. Hybridization of ³H—cDNA with rRNA from other types of bacteria (taxonomic Class Schizomytes) | A. | Member of the Family Enterobacteraceae | |
| | | 1. *Escherischia coli* (infects mammals) | 52% |
| | B. | Member of the Family Legionellaceae | |
| | | 1. *Legionella pneumophila* (infects man) | >28% |
| | C. | Member of the Family Micrococcaceae | |
| | | 1. *Micrococcus luteus* | 50–60% |
| | | 2. *Staphylococcus aureus* | >50% |
| | D. | Member of the Family Lactobacillaceae | |
| | | 1. *Streptococcus faecalis* | >50% |
| | E. | Member of the Family Bacillaceae | |
| | | 1. *Bacillus subtilis* | >40% |
| IV. Hybridization of ³H—cDNA with rRNA from a Yeast | | | >2% |
| V. Hybridization of ³H—cDNA with | | Human (primate) | <1% |
| | | Cow (bovine) | <1% |

TABLE 4-continued
Hybridization of Selected Mollicutes $^3$H—cDNA with rRNA from Widely Different Sources

| | Source of rRNA | Percent Hybridization of $^3$H—cDNA with rRNA |
|---|---|---|
| rRNA from mammals and a bird. | Mouse (rodent) | <1% |
| | Rat (rodent) | <1% |
| | Hamster (rodent) | <1% |
| | Rabbit (lagomorph) | <1% |
| | Chicken (avian) | <1% |

Excess rRNA hybridizations are done at 68° C., 0.48 M PB. Hybridization assays are done with hydroxyapatite at 67° C. in 0.14 M PB, 0.005% sodium dodecyl sulfate. The hybridization exposure is sufficient to ensure complete reaction of the $^3$H—cDNA with nuclear rRNA or for mitochondrial rRNA. Non-bacterial rRNA Cot's of at least $2 \times 10^3$ are reached in the case of the mammals and bird. A non-specific signal of 1-2 percent has been subtracted from the hybridization values presented above.

TABLE 5
Detection and Quantitation of Mollicutes in Tissue Culture Cells

| Cell Line | Hybridization Time (hours) | Percent Hybridization of $^3$H—cDNA with RNA | Number of Bacteria Detected |
|---|---|---|---|
| 1. 44-2C (rat) | 17 | <1 | None detected |
| | 40 | <1 | None detected |
| 2. P388 D1M (mouse) | 1.1 | <1 | None detected |
| | 22.5 | <1 | None detected |
| 3. P388 D1C (mouse) | 0.025 | 20 | $5 \times 10^7$ |
| | 16.2 | 78 | (about 1 Mollicute per mammalian cell) |

Excess rRNA Hybridizations are done at 68° C. in 0.48 M PB in a volume of 0.01 to 0.04 ml. Each mixture contains $2 \times 10^5$ micrograms of $^3$H—cDNA probe and 50-200 micrograms of sample RNA.

Quantitation of rRNA by Nucleic Acid Hybridization

The amount of bacterial rRNA present in a sample can be determined by measuring the kinetics of hybridization of the selected $^3$H-cDNA probe with the RNA isolated from a tissue sample and comparing these kinetics to those of a known standard mixture. This can be done even in the presence of a large excess of mammalian cell rRNA since the probe does not hybridize with this rRNA (see Table 4,V).

For measuring the kinetics, the hybridization mixtures contain, $10^{-5}$ to $10^{-4}$ micrograms of $^3$H-cDNA and 1 to $10^3$ micrograms of purified sample RNA in 0.01 to 0.1 ml of 0.48 M PB. This mixture is incubated at 68° C. and aliquots are removed, diluted to 0.14 M PB and assayed for hybridization at various times after the initiation of the reaction. Hybridization assays are performed using hydroxyapatite as described earlier. The results obtained are compared to the hybridization kinetics of the probe reacted with standard RNAs containing known amounts of bacterial rRNA. These standards are mixtures of mammalian cell RNA and known amounts of a specific bacterial rRNA.

Detection and Quantitation of Members of the Class Mollicutes in Tissue Culture Cells Table 5 presents data obtained by hybridizing the selected probe with RNA isolated (as described earlier) from three different tissue culture cell samples. Only cell line number 3 is detectably contaminated and the kinetics of the reaction indicate that about $5 \times 10^7$ bacterial cells are present in the tissue culture cells.

The following example is another embodiment of the method of my invention, used for detecting very small numbers, even one trypanosome, in the presence of a large number of blood cells.

The detection of trypanosomes is important since certain members of the protozoan group Trypanosoma are pathogenic for humans, causing diseases that include East African sleeping sickness, West African sleeping sickness, and South American trypanosomiasis. These organisms are large and have varying characteristic shapes, depending on the stage of the life cycle. Prior art methods rely mainly on serologic, differential staining coupled with microscopic examination and animal inoculation procedures for detecting these organisms in humans. The serodiagnostic methods vary in sensitivity and specificity and may be difficult to interpret. The microscopic methods are most used, however small numbers of the trypanosomes are often difficult to detect in the presence of large numbers of blood cells. Animal inoculation is a long and costly procedure.

The embodiment of the invention set forth in the example following is a method which makes it relatively easy to detect the presence of one trypanosome even when co-present with a large number of blood cells.

EXAMPLE II
Production of Radioactive DNA Complementary to Trypanosome rRNA

Radioactive DNA complementary ($^3$H-cDNA) to Trypanosoma brucei rRNA is produced in the same way as M. hominis $^3$H-cDNA, which is described above in detail, except that Trypanosoma b. rRNA is used as a template.

Selection of Trypanosome ³H-cDNA Which is Complementary to Trypanosome rRNA but is not Complementary to Human rRNA This is done in the same way as described earlier for *M. hominis* except that *Trypanosoma b.* ³H-cDNA is hybridized to the human rRNA.

Use of Selected Trypanosome ³H-cDNA to Detect and Quantitate Trypanosomes in Human Tissue or Fluid The production of the selected ³H-cDNA probe allows the detection and quantitation of trypanosomes in human samples by detecting the presence of trypanosome rRNA. A necessary requirement of such a test is that the selected probe must not hybridize to rRNA from human cells which do not contain trypanosomes. Table 7 shows that this requirement is met.

TABLE 7

Hybridization of Selected *Trypanosoma brucei* ³H—cDNA with rRNA from Different Sources

| rRNA Source | Percent Hybridization of ³H—cDNA with rRNA |
|---|---|
| No RNA added | <1% |
| *Trypanosome brucei* rRNA | 98% |
| Bacterial (*Mycoplasma hominis*) rRNA | <1% |
| Human rRNA | <1% |
| Human rRNA known to be contaminated with *Trypanosome brucei* | 98% |

Excess rRNA hybridizations are done at 65° C. in 0.48 M PB. Reactions are run for 24 hours and the hybridization exposure is sufficient to ensure complete reaction of the human nuclear or mitochondrial rRNAs and the bacterial rRNA. Hybridization assays are done with hydroxyapatite at 72° C. in 0.14 M PB, 0.005% sodium dodecyl sulfate.

The publications listed below are of interest in connection with various aspects of the invention and are incorporated herein as part of the disclosure.

1. Repeated Sequences in DNA. R. J. Britten and D. E. Kohne, Science (1968) 161 p 529.
2. Kinetics of Renaturation of DNA. J. G. Wetmur and N. Davidson, J. Mol. Biol. (1968) 31 p 349.
3. Hydroxyapatite Techniques for Nucleic Acid Reassociation. D. E. Kohne and R. J. Britten, in Procedures in Nucleic Acid Research (1971). eds Cantoni and Davies, Harper and Row Vol 2, p 500.
4. Hybridization of Denatured RNA and Small DNA Fragments Transferred to Nitrocellulose. P. S. Thomas, Proc. Natl. Acad. Sci. USA (1980) 77 p 5201.
5. DNA-DNA Hybridization on Nitrocellulose Filters: General Considerations and Non-Ideal Kinetics. R. Flavell el al., Eur. J. Biochem. (1974) 47 p 535.
6. Assay of DNA-RNA Hybrids by S₁ Nuclease Digestion and Adsorption to DEAE-Cellulose Filters. I. Maxwell et al., Nucleic Acids Research (1978) 5 p 2033.
7. Molecular Cloning: A Laboratory Manual. T. Maniatis et al., Cold Spring Harbor Publication (1982).
8. Efficient Transcription of RNA into DNA by Avian Sarcoma Virus Polymerase. J. Taylor et al., Biochemica et Biophys. Acta (1976) 442 p 324.
9. Use of Specific Radioactive Probes to Study Transcription and Replication of the Influenza Virus Genome. J. Taylor et al., J. Virology (1977) 21 #2, p 530.
10. Virus Detection by Nucleic Acid Hybridization: Examination of Normal and ALs Tissue for the Presence of Poliovirus. D. Kohne et al., Journal of General Virology (1981) 56 p 223-233.
11. Leukemogenesis by Bovine Leukemia Virus. R. Kettmann et al., Proc. Natl. Acad. Sci. USA (1982) 79 #8 p 2465-2469.
12. Prenatal Diagnosis of α Thalassemia: Clinical Application of Molecular Hybridization. Y. Kan et al., New England Journal of Medicine (1976) 295 #21 p 1165-1167.
13. Gene Deletions in α Thalassemia Prove that the 5' Locus is Functional. L. Pressley et al., Proc. Natl. Acad. Sci. USA (1980) 77 #6 p 3586-3589.
14. Use of Synthetic Oligonucleotides as Hybridization Probes. S. V. Suggs et al., Proc. Natl. Acad. Sci. USA (1981) 78 p 6613.
15. Identification of Enterotoxigenic *E. coli* by Colony Hybridization Using 3 Enterotoxin Gene Probes. S. L. Mosely et al., J. of Infect. Diseases (1982) 145 #6 p 863.
16. DNA Reassociation in the Taxonomy of Enteric Bacteria D. Brenner, Int. J. Systematic Bacteriology (1973) 23 #4 p 298-307.
17. Comparative Study Ribosomal RNA Cistrons in Enterobacteria and Myxobacteria. R. Moore et al., J. Bacteriology (1967) 94 p 1066-1074.
18. Ribosomal RNA Similarities in the Classification of Rhodococcus and Related Taxa. M. Mordarski et al., J. General Microbiology (1980) 118 p 313-319.
19. Retention of Common Nucleotide Sequences in the Ribosomal RNA DNA of Eukaryotes and Some of their Physical Characteristics. J. Sinclair et al., Biochemistry (1971) 10 p 2761.
20. Homologies Among Ribosomal RNA and Messenger RNA Genes in Chloroplasts, Mitochondria and *E. coli*. H. Bohnert et al., Molecular and General Genetics (1980) 179 p 539-545.
21. Heterogeneity of the Conserved Ribosomal RNA Sequences of *Bacillus subtilis*. R. Doi et al., J. Bacteriology (1966) 92 #1 p 88.
22. Isolation and Characterization of Bacterial Ribosoma RNA Cistrons. D. Kohne, Biophysical Journal (1968) 8 #10 p 1104-1118.
23. Taxonomic Relations Between Archaebacteria Including 6 Novel Genera Examined by Cross Hybridization of DNAs and 16S rRNAs. J. Tu et al., J. Mol. Evol. (1982) 18 p 109.
24. rRNA Cistron Homologies Among Hyphomicrobium and Various Other Bacteria. R. Moore, Canadian J. Microbiology (1977) 23 p 478.

As used in the specification and claims the following terms are defined as follows:

DEFINITION OF TERMS base (see nucleotide)
base pair mismatches
(see imperfectly complementary
base sequence)
base sequence, (nucleotide
sequence or gene sequence

DEFINITION OF TERMS -continued

| | |
|---|---|
| or polynucleotide sequence or single strand nucleic acid sequence) | A DNA or RNA molecule consisting of multiple bases. |
| complementary base pairs | Certain of the bases have a chemical affinity for each other and pair together or are complementary to one another. The complementary base pairs are A:T and G:C in DNA and A:U and G:C in RNA. |
| complementary strands or complementary base sequences | Perfectly complementary nucleic acid molecules are nucleic acid molecules in which each base in one molecule is paired with its complementary base in the other strand, to form a stable helical double strand molecule. The individual strands are termed complementary strands. |
| criterion | Most precisely defined as the difference between the temperature of melting of the double strand nucleic acid and the temperature at which hybridization is done. The melting temperature of a double strand nucleic acid is determined primarily by the salt concentration of the solution. The criterion determines the degree of complementarity needed for two single strands to form a stable double strand molecule. The criterion can be described as highly stringent, stringent, or not very stringent. A highly stringent criterion requires that two interacting complementary sequences be highly complementary in sequence in order to form a stable double strand molecule. A poorly stringent criterion is one which allows relatively dissimilar complementary strands to interact and form a double strand molecule. High stringency allows the presence of only a small fraction of base pair mismatches in a double strand molecule A poorly stringent criterion allows a much larger fraction of base pair mismatches in the hybridization product. |
| denatured or dissociated nucleic acid | The bonds between the paired bases in a double strand nucleic acid molecule can be broken, resulting in two single strand molecules, which then diffuse away from each other. |
| double strand nucleic acid | As it is found in the cell, most DNA is in the double strand state. The DNA is made up of two DNA molecules or strands wound helically around each other. The bases face inward and each base is specifically bonded to a complementary base in the other strand. For example, an A in one strand is always paired with a T in the other strand, while a G in one strand is paired with a C in the other strand. In a bacterial cell the double strand molecule is about $5 \times 10^6$ base pairs long. Each of the bases in one strand of this molecule is paired with its base complement in the other strand. The base sequences of the individual double strand molecules are termed complementary strands. |
| hybridization (see nucleic acid hybridization) | |
| imperfectly complementary base sequences (base pair mismatches) | Stable double strand molecules can be formed between two strands where a fraction of the bases in the one strand are paired with a non-complementary base in the other strand. |
| marked probe or marked sequence | Single strand nucleic acid molecules which are used to detect the presence of other nucleic acids by the process of nucleic acid hybridization. The probe molecules are marked so that they can be specifically detected. This is done by incorporating a specific marker molecule into the nucleic acid |

-continued

| DEFINITION OF TERMS | |
|---|---|
| | or by attaching a specific marker to the nucleic acid. The most effective probes are marked, single strand sequences, which cannot self hybridize but can hybridize only if the nucleic acid to be detected is present. A large number of different markers are available. These include radioactive and fluorescent molecules. |
| nucleic acid hybridization or hybridization, (reassociation, or renaturation) | The bonds between the two strands of a double strand molecule can be broken and the two single strands can be completely separated from each other. Under the proper conditions the complementary single strands can collide, recognize each other and reform the double strand helical molecule. This process of formation of double strand molecules from complementary single strand molecules is called nucleic acid hybridization. Nucleic acid hybridization also occurs between partially complementary single strands |
| nucleotide, nucleotide base or base | Most DNA consists of sequences of only four nitrogeneous bases: adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U). |
| reassociation | (see nucleic acid hybridization) |
| renaturation | (see nucleic acid hybridization) |
| ribosomal RNA or rRNA | The RNA which is present in ribosomes. Virtually all ribosomes contain 3 single strand RNA subunits: one large, one medium sized, and one small. |
| ribosome | A cellular particle (containing RNA and protein) necessary for protein synthesis. All life forms except viruses contain ribosomes. |
| rRNA DNA or rRNA gene | The base sequence in the DNA which codes for ribosomal RNA. Each rRNA subunit is coded for by a separate gene. |
| rRNA probe | A marked nucleic acid sequence which is complementary to rRNA and therefore will hybridize with rRNA to form a stable double strand molecule. |
| thermal stability of double strand nucleic acid molecules | The thermal stability or melting temperature is the temperature at which half of a population of double strand molecules has been converted to the single strand form. |
| restriction enzymes | Components of the restriction-modification cellular defense system against foreign nucleic acids. These enzymes cut unmodified (e.g., methylated) double-stranded DNA at specific sequences which exhibit twofold symmetry about a point. |

While the invention has been described in detail for purposes of illustration, and to meet the requirements of 35 USC 112, it will be apparent to those skilled in the art that changes and modifications therein are included without departing from the spirit and scope of the invention.

What is claimed is:

1. A method for detecting the presence in a test sample of any non-viral organisms belonging to a group, said group consisting of at least one but less than all non-viral organisms, which comprises:
   (a) bringing together any test sample rRNA and a nucleic acid probe, said probe having been selected to be sufficiently complementary to hybridize to one or more rRNA subunit subsequences that are specific to said group of non-viral organisms and to be shorter in length than the rRNA subunit to which said probe hybridizes;
   (b) incubating the probe and any test sample rRNA under specified hybridization conditions such that said probe hybridizes to the rRNA of said group of non-viral organisms and does not detectably hybridize to rRNA from other non-viral organisms; and, (c) assaying for hybridization of said probe to any test sample rRNA.

2. The method of claim 1 wherein said probe that is sufficiently complementary is perfectly complementary.

3. The method of claim 1 wherein said probe that is sufficiently complementary is not perfectly complementary.

4. The method of claim 1 further comprising the use of one or more additional probes which are sufficiently complementary to hybridize to one or more additional rRNA subunit subsequences that are specific to said group of non-viral organisms.

5. The method of claim 1 wherein said probe is labelled.

6. The method of claim 1 wherein said non-viral organisms are bacteria.

7. The method of claim 6 wherein said bacteria are Mollicutes.

8. The method of claim 1 wherein said non-viral organisms are protozoa.

9. The method of claim 8 wherein said protozoa are Trypansoma.

10. The method of claim 1 wherein said nucleic acid probe is sufficiently complementary to detectably hybridize to one or more rRNA subunit subsequences of said group of non-viral organisms and to rRNA subunit subsequences of one or more non-viral organisms which are not members of said group, and said test sample is selected to be substantially free of said non-viral organisms which are not members of said group.

11. A method for determining the presence or amount of a specific group of non-viral organisms consisting of at least one but less than all non-viral organisms, which comprises:
   (a) mixing a nucleic acid probe with a test sample, said probe having been selected to have a sequence shorter in length than the rRNA subunit sequence to which it hybridizes, and to be capable of hybridizing with one or more rRNA subunit subsequences present in the group of non-viral organisms whose presence or amount is to be determined and not capable under conditions of the method of detectably hybridizing with the rRNA of other non-viral organisms;
   (b) placing the mixture under conditions such that hybridization between said probe and said rRNA subunit subsequences will occur, and;
   (c) assaying the mixture for hybridization between said probe and said rRNA subunit subsequences.

12. The method of claim 11 wherein said probe is perfectly complementary to at least one rRNA subunit subsequence present in the group of non-viral organisms whose presence or amount is to be determined.

13. The method of claim 11 wherein said probe is not perfectly complementary to one or more rRNA subunit subsequences present in the group of non-viral organisms whose presence or amount is to be determined.

14. The method of claim 11 further comprising the use of one or more additional probes which are capable of hybridizing with one or more additional rRNA subunit subsequences present in the group of non-viral organisms whose presence or amount is to be determined.

15. The method of claim 11 wherein said probe is labelled.

16. The method of claim 11 wherein said non-viral organisms are bacteria.

17. The method of claim 16 wherein said bacteria are Mollicutes.

18. The method of claim 11 wherein said non-viral organisms are protozoa.

19. The method of claim 18 wherein said protozoa are Trypansoma.

20. The method of claim 11 wherein said nucleic acid probe is capable of detectably hybridizing with one or more rRNA subunits subsequences of the group of non-viral organisms whose presence or amount is to be determined and to rRNA subunit subsequences of one or more non-viral organisms which are not members of said group, and said test sample is selected to be substantially free of said non-viral organisms which are not members of said group.

21. The method of claim 11 further comprising the step of estimating or quantitating the number of said rRNA subunit subsequences in said test sample.

22. The method of claim 11 further comprising the step of estimating or quantitating the number of said non-viral organisms in said test sample and/or the source of said test sample.

23. A method for determining the presence or amount in a test sample of any non-viral organisms belonging to a group, said group consisting of at least one but less than all non-viral organisms, which comprises:
   (a) bringing together any test sample rRNA and a nucleic acid probe, said probe having been selected to be sufficiently complementary to hybridize to one or more rRNA subunit subsequences of said group of non-viral organisms and to be shorter in length than the rRNA subunit which said probe hybridizes;
   (b) incubating the probe and any test sample rRNA under specified hybridization conditions such that said probe hybridizes to a detectably greater extent with the rRNA of said group of non-viral organisms than it does with the rRNA from other non-viral organisms, and;
   (c) assaying for hybridization of said probe to any test sample rRNA.

24. The method of claim 23 further comprising the step of estimating or quantitating the number of said rRNA subunit subsequences of said group of non-viral organisms in said test sample.

25. The method of claim 23 further comprising the step of estimating or quantitating the number of said non-viral organisms belonging to a group in said test sample and/or the source of said test sample.

26. A method for detecting the presence in a test sample of any non-viral organisms belonging to a group, said group consisting of at least one non-viral organism, which comprises:
   (a) bringing together any test sample rRNA and a plurality of nucleic acid probes said probes having been selected to be sufficiently complementary to hybridize to one or more rRNA subunit subsequences that are specific to said group of non-viral organisms and each of said probes to be shorter in length than the rRNA subunit to which each of said probes hybridizes;
   (b) incubating the probes and any test sample rRNA under specified hybridization conditions such that said probes hybridize to the rRNA of said group of non-viral organisms and do not detectably hybridize to rRNA from other non-viral organisms; and,
   (c) assaying for hybridization of said probes to any test sample rRNA.

27. The method of claim 26 wherein one or more of said probes that are sufficiently complementary are perfectly complementary.

28. A method for determining the presence or amount of a specific group of non-viral organisms consisting of at least one non-viral organism, which comprises:
(a) mixing a plurality of nucleic acid probes with a test sample, each of said probes having been selected to have a sequence shorter in length than the rRNA subunit sequence to which each of said probes hybridizes, and to be capable of hybridizing with one or more rRNA subunit subsequences present in the group of non-viral organisms whose presence or amount is to be determined and not capable under conditions of the method of detectably hybridizing with the rRNA of other non-viral organisms;
(b) placing the mixture under conditions such that hybridization between said probes and said rRNA subunit subsequences will occur; and,
(c) assaying the mixture for hybridization between said probes and said rRNA subunit subsequences.

* * * * *